(12) United States Patent
Naito

(10) Patent No.: US 7,713,554 B2
(45) Date of Patent: May 11, 2010

(54) USE OF ENHANCED WATER TO IMPROVE BLOOD SUGAR MANAGEMENT

(75) Inventor: Harusuke Naito, Oneonta, NY (US)

(73) Assignee: Wellness Enterprises, LLC, Gainesville, FL (US)

( * ) Notice: Subject to any disclaimer, the term of this patent is extended or adjusted under 35 U.S.C. 154(b) by 663 days.

(21) Appl. No.: 11/070,103

(22) Filed: Mar. 1, 2005

(65) Prior Publication Data

US 2005/0191364 A1    Sep. 1, 2005

Related U.S. Application Data

(60) Provisional application No. 60/549,235, filed on Mar. 1, 2004.

(51) Int. Cl.
*A61K 33/24* (2006.01)
*A61K 33/00* (2006.01)
*A61K 33/06* (2006.01)
*A61P 3/10* (2006.01)

(52) U.S. Cl. .................. 424/646; 424/600; 424/617; 424/681; 424/682; 424/724; 514/866

(58) Field of Classification Search ................ 514/866; 424/600, 617, 646, 681, 682, 724
See application file for complete search history.

(56) References Cited

U.S. PATENT DOCUMENTS

| | | | |
|---|---|---|---|
| 3,536,197 A | 10/1970 | Ward | |
| 4,094,779 A | 6/1978 | Behrman | |
| 4,455,236 A | 6/1984 | Kim | |
| 4,642,192 A | 2/1987 | Heskett | |
| 4,871,555 A | 10/1989 | Schwartz et al. | |
| 5,002,665 A | 3/1991 | Brueggemann | |
| 5,122,274 A | 6/1992 | Heskett | |
| 5,135,654 A | 8/1992 | Heskett | |
| 5,198,118 A | 3/1993 | Heskett | |
| 5,269,932 A | 12/1993 | Heskett | |
| 5,275,737 A | 1/1994 | Heskett | |
| 5,314,623 A | 5/1994 | Heskett | |
| 5,415,770 A | 5/1995 | Heskett | |
| 5,433,856 A | 7/1995 | Heskett | |
| 5,510,034 A | 4/1996 | Heskett | |
| 5,575,904 A | 11/1996 | Suzuki | |
| 5,599,454 A | 2/1997 | Heskett | |
| 5,628,900 A | 5/1997 | Naito | |
| 5,698,028 A * | 12/1997 | Higa | ............ 71/11 |
| 5,795,471 A | 8/1998 | Naito | |
| 5,833,859 A | 11/1998 | Heskett | |
| 5,951,869 A | 9/1999 | Heskett | |
| 6,129,841 A | 10/2000 | Dann | |
| 6,197,204 B1 | 3/2001 | Heskett | |
| 6,449,990 B1 * | 9/2002 | Kawajiri et al. | ............ 68/17 R |

FOREIGN PATENT DOCUMENTS

JP    62123124 A    6/1987
JP    2003275328 A    9/2003

OTHER PUBLICATIONS

Amiri, M.C. et al., "On reduction in the surface tension of water due to magnetic treatment," Colloids and Surfaces A: Physicochem. Eng. Aspects, vol. 278, pp. 252-255 (2006).*
Quickenden, T.I. et al., "The effect of magnetic fields on the pH of water," The Journal of Physical Chemistry, vol. 75(18), pp. 2830-2831 (1971).*
Yamashita, M. et al., "Direct current magnetic field and electromagnetic field effects on the pH and Oxidation-Reduction Potential equilibrium rates of water . . ." Langmuir, vol. 19, pp. 6851-6856 (2003).*
National Diabetes Information Clearinghouse (NDIC). Prevent diabetes problems: Keep your diabetes under control. Feb. 2008. [retrieved on Aug. 2, 2008]. Retrieved from the Internet<URL: http://diabetes.niddk.nih.gov/dm/pubs/complications_control/>.*
Kiseki Museum photo of Bakuhanseki [retrieved on Apr. 27, 2009]. Retrieved from the Internet: <URL: www.kiseki-jp.com/english/stone-information/collection/collections/bakuhanseki.html>.*
Britannica Online Encyclopedia, online article on "unit of measurement" [retrieved on Dec. 17, 2009]. Retrieved from the Internet:<URL: http://www.britannica.com/EBchecked/topic/227199/gauss>.*
MEDLINE abstract, accession No. 1985102499 (1985).*
BIOSIS abstract, accession No. 1980:257769 (1979).*
Muto, H. et al., "Filtering effects to bacteria and improvement of water quality by granite porphyry materials," Water Research, vol. 30(2), pp. 400-404 (1996).*

(Continued)

*Primary Examiner*—John Pak
(74) *Attorney, Agent, or Firm*—Saliwanchik, Lloyd & Saliwanchik

(57) ABSTRACT

The subject invention provides a process and apparatus for making "enhanced water" that is uniquely suitable for improving circulation, hydration and insulin usage with diabetics. Thus, in a preferred embodiment, the invention provides methods for the treatment and/or prevention of diabetes as well as the prevention or delay in development of diabetes-related complications, conditions or diseases.

9 Claims, No Drawings

OTHER PUBLICATIONS de Valk, H.W. et al., "Oral magnesium suplementation in insulin-requiring patients with Type 2 diabetes mellitus," Atherosclerosis, vol. 115, supplement 1, S53 (1995).*

Ise et al., "Effect of Far-Infrared Radiation on Forearm Skin Blood Flow," *Ann. Physiol. Anthrop.*, 1987, vol. 6, No. 1, pp. 31-32.

Ogita et al., "Effects of Far-Infrared Radiation on Lactation," *Ann. Physiol. Anthrop.*, 1990, vol. 9, No. 2, pp. 83-91.

Yu et al., "Biological effect of far-infrared therapy on increasing skin microcirculation in rats," *Photodermatol. Photoimmunol. Photomed.*, 2006, vol. 22, pp. 78-86.

Carlo, G. I. and C.J. Mettlin "Cancer Incidence and Trihalomethane Concentration in a Public Drinking Water System" *Am. J. Pub. Health*, 1980, pp. 523-524, vol. 70, No. 5.

Committee on Drinking Water Contaminants "Excerpts From the Executive Summary for Classifying Drinking Water Contaiminants for Regulatory Consideration" *National Academy Press*, 2001, pp. 1-8.

Craun, G. F. "Epidemiologic Studies of Organic Micropollutants in Drinking Water" *Sci. Total Environ.*, 1985, pp. 461-472, vol. 47.

Daniel, F. B. et al. "Comparative Subchronic Toxicity Studies of Three Disinfectants" *J. Amer. Water Works Assoc.*, 1990, pp. 61-69, vol. 82.

King et al. "Case-Control Study of Colon and Rectal Cancers and Chlorination By-Products in Treated Water" *Cancer Epidem.*, 2000, pp. 813-818, vol. 9.

Lee, S. H. et al. "Surveillance for Waterborne-Disease Outbreaks—United States, 1999-2000" *Morbidity and Mortality Weekly Report Surveillance Summaries*, 2002, pp. 1-47, vol. 51, No. 8.

National Toxicology Program "NTP Toxicology and Carcinogenesis Studies of Chlorinated Water (CAS Nos. 7782-50-5 and 7681-52-9) and Chloraminated Water (CAS No. 10599-90-3) (Deionized and Charcoal-Filtered) in F344/N Rats and B6C3F1 Mice (Drinking Water Studies)" *Nat. Toxicol. Program Tech. Rep. Ser.*, 1992, pp. 1-466, vol. 392.

* cited by examiner

USE OF ENHANCED WATER TO IMPROVE BLOOD SUGAR MANAGEMENT

CROSS-REFERENCE TO A RELATED APPLICATION

This application claims the benefit of U.S. Provisional Application Ser. No. 60/549,235, filed Mar. 1, 2004, which is hereby incorporated by reference in its entirety.

BACKGROUND OF THE INVENTION

Diabetes is a chronic disease that has no cure. It is estimated that about 18.2 million people, or 6.3 percent of the population, in the United States have diabetes. While roughly 13 million have been diagnosed, it is believed that 5.2 million people are not aware that they have the disease. As the sixth leading cause of death by disease in 2000, diabetes is costing the US health care system an estimated $132 billion annually; according to the National Diabetes Information Clearinghouse, NIH Publication No. 04-3892, November 2003. More serious than the economic costs associated with diabetes are the decrease in quality of life, serious health complications/consequences, and deaths associated with diabetes.

With about 12,000 to 24,000 new cases each year, diabetes is the leading cause of new cases of blindness in adults ages 20-74. Diabetes is also the leading cause of end-stage renal disease, accounting for about 44 percent of new cases annually. In 2001 alone, approximately 42,800 people initiated treatment for end stage renal disease (kidney failure) because of diabetes. About 60-70 percent of people with diabetes have mild to severe forms of diabetic nerve damage, which, in severe forms, can lead to lower limb amputations. In fact, more than 60 percent of non-traumatic, lower limb amputations are performed on persons with diabetes. In 2002-2003, about 82,000 non-traumatic, lower limb amputations were performed on persons with diabetes. People with diabetes are 2 to 4 times more likely to suffer a stroke. Moreover, adults with diabetes have heart disease death rates about 2 to 4 times higher than those without diabetes.

Diabetes is a group of diseases characterized by high blood glucose levels, which result from defects in insulin production, insulin action, or both. Because diabetes can remain undiagnosed for years, many people become aware that they have diabetes only after the development of one of its life-threatening complications. Although the exact etiology of diabetes is still unknown, it is well-accepted that both genetics and environmental factors, such as obesity and lack of exercise, are important factors.

One type of diabetes, Type 1 (or insulin-dependent diabetes mellitus or juvenile-onset diabetes), develops when the body's immune system destroys pancreatic cells that make the hormone insulin, which regulates blood glucose levels. Type 1 diabetes usually occurs in children and young adults; although disease onset can occur at any age. Type 1 diabetes accounts for about 5 to 10 percent of all diagnosed cases of diabetes. Risk factors for Type 1 diabetes include autoimmune, genetic, and environmental factors. Individuals diagnosed with Type 1 diabetes require daily delivery of insulin via injections or pumps.

Another type of diabetes, Type 2 (or non-insulin-dependent diabetes mellitus or adult-onset diabetes), is a metabolic disorder resulting from the body's inability to make enough, or properly use, insulin. This disease usually begins as insulin resistance, a disorder in which the cells do not use insulin properly, and as the need for insulin rises, the pancreas gradually loses its ability to produce insulin. Type 2 diabetes is the most common form of the disease accounting for 90-95 percent of diabetes. Type 2 diabetes is nearing epidemic proportions, due to an increased number of older Americans, and a greater prevalence of obesity and a sedentary lifestyle.

Gestational diabetes refers to a form of glucose intolerance that occurs in pregnant women. During pregnancy, gestational diabetes requires treatment to normalize maternal blood glucose levels to avoid complications in the infant. A percentage (5-10 percent) of women with gestational diabetes have Type 2 diabetes after pregnancy. Women who have had gestational diabetes also have a 20-50 percent chance of developing diabetes in the next 5-10 years.

Hyperinsulinemia refers to the overproduction of insulin by pancreatic cells. Often, hyperinsulinemia occurs as a result of insulin resistance, which is a condition defined by cellular resistance to the action of insulin. Insulin resistance, as defined above, is a state/disorder in which a normal amount of insulin produces a subnormal biologic (metabolic) response. For example, in insulin-treated patients with diabetes, insulin resistance is considered to be present whenever the therapeutic dose of insulin exceeds the secretory rate of insulin in normal person.

Impaired glucose homeostasis (or metabolism) refers to a condition in which blood sugar levels are higher than normal but not high enough to be classified as diabetes. There are two categories that are considered risk factors for future diabetes and cardiovascular disease. Impaired glucose tolerance (IGT) occurs when the glucose levels following a 2-hour oral glucose tolerance test are between 140 to 199 mg/dl. IGT is a major risk factor for type 2 diabetes and is present in about 11 percent of adults, or approximately 20 million Americans. About 40-45 percent of persons age 65 years or older have either type 2 diabetes or IGT. Impaired fasting glucose (IFG) occurs when the glucose levels following an 8-hour fasting plasma glucose test are greater than 110 but less than 126 mg/dl.

Hyperglycemia, a common feature of diabetes, is caused by decreased glucose utilization by liver and peripheral tissues and an increased glucose production by liver. Glucokinase (GK), the major glucose phosphorylating enzyme in the liver and the pancreatic β-cells, plays an important role in regulating blood glucose homeostasis. Notably, the levels of this enzyme are lowered in patients with type 2 diabetes (Caro, J. F. et al., *Hormone metabolic Res.*, 27; 19-22, 1995) and in some diabetic animal models (Barzilai, N. and Rossetti, L. *J. Biol. Chem.*, 268:25019-25025, 1993).

Many pharmaceutical compositions and methods have been proposed to treat diabetes. For example, one approach to reducing hyperglycemia in diabetes involves increasing liver GK activity (Van Schaftingen, E. et al., *Adv. Enzyme Regul.* 32:133-148, 1992). Studies involving transgenic diabetic mice have shown that increased GK copy number results in increased hepatic glucose metabolism and decreased plasma glucose levels (Ferre, T. et al., *Proc. Natl. Acad. Sci. USA*, 93:7225-7230 (1996a) and *FASEB J*, 10:1213-1218, (1996b); Niswender, K. D. et al., *J. Biol. Chem.*, 272:22570-22575 (1997)), demonstrating that increasing liver GK may be effective in reducing hyperglycemia in diabetes. In addition, Hariharan, N. et al. (*Diabetes* 46:11-16 (1997)) have demonstrated that increasing liver GK improves glucose homeostasis and leads to weight reduction in transgenic mice.

The two pharmacological modalities presently used to lower blood sugar are oral hypoglycemic (anti-diabetic) agents and insulin. Insulin replacement is presently accomplished by injection and is based upon the lack of insulin or limitation of its action in diabetes. Oral anti-diabetic agents are not chemically akin to insulin and their sugar-lowering mechanism differs from the action of direct insulin replacement. Oral hypoglycemic agents and insulin are, at present, therapeutically utilized alone or in concert with each other, according to the needs of the diabetic individual. Some individuals are best treated with more than one oral agent, with, or without insulin.

For the foregoing reasons, there is a need for new therapeutic treatments for diabetes; particularly for eliminating or reducing symptoms related to diabetes.

Wellness Enterprises manufactures and sells a well-known water filtration and enhancement system that removes contaminants and also temporarily changes the properties of water by using certain "enhancing media". The temporary changes in properties that have been observed include 1) an increase in wetness (e.g., increased penetration of membranes), 2) an increase in solubility (both solids and gases), 3) the release of certain trace minerals most notably silica, magnesium, yttrium, vanadium and titanium, and 4) the release of stabilized negative ions. To date, there has been no suggestion of utilizing this enhanced water to treat metabolic disorders such as diabetes.

BRIEF SUMMARY OF THE INVENTION

The subject invention provides a process and apparatus for making "enhanced water" that is uniquely suitable for improving circulation, hydration and/or metabolic indices, in particular to improve glucose metabolism for blood sugar management. The subject invention contemplates decreasing glucose intolerance; decreasing hyperinsulinemia; decreasing insulin resistance; and/or decreasing hyperglycemia or hypoglycemia. Thus, in a preferred embodiment, the invention provides methods for the treatment and/or prevention of diabetes as well as the prevention or delay in development of diabetes-related complications, conditions or diseases.

Specifically exemplified herein is the use of an enhanced water to reduce and/or eliminate the severity, intensity, and/or duration of at least some complications associated with diabetes. For example, complications, conditions and diseases such as background diabetic retinopathy, macular edema, cataracts, necrobiosis lipoidica, diabetic dermopathy, fungal infections, congestive heart failure, kidney disease, diabetic neuropathy, which are commonly associated with diabetes, can be reduced through consumption, according to the subject invention, of enhanced water, as described herein.

In preferred embodiment of the invention, enhanced water is administered to a patient diagnosed with diabetes to treat diabetes and/or improve insulin usage and/or decrease the severity of diabetes-related complications. In a related embodiment, enhanced water is administered in combination with other known agents that are used to treat diabetes (i.e., insulin, sulfonylureas, biguanides, α-glucosidase inhibitors, thiazolidinediones, meglitinides, D-phenylalanine) to either prevent and/or treat diabetes and diabetes-related complications.

Further advantages of the subject invention include reducing or ameliorating one or more aberrant indices associated with metabolism disorders (such as reducing glucose intolerance, reducing insulin resistance, reducing glucose intolerance, reducing insulin resistance, reducing hyperglycemia, reducing hypoglycemia, reducing hyperinsulinemia, and treating and/or preventing the development of diabetes). In accordance with the subject invention, administration of enhanced water to a patient prior to or at the onset of diabetes diagnosis can alter the patient's metabolism so that diabetes does not develop, or develops to a lesser extent than would be observed in the absence of the enhanced water.

In accordance with the subject invention, the daily dosage amount of an enhanced water administered to a patient diagnosed with diabetes or suffering from complications, conditions, or diseases associated with diabetes can be, for example, about six to ten 8-ounce servings.

DETAILED DISCLOSURE OF THE INVENTION

The subject invention provides a process and apparatus for making "enhanced water" that is uniquely suitable for improving circulation, hydration and/or metabolic indices in a patient. In particular, the subject invention provides methods for reducing glucose intolerance, reducing insulin resistance, reducing hyperglycemia, reducing hyperinsulinemia, reducing hypoglycemia, and/or improving insulin usage with diabetics. Thus, in a preferred embodiment, the invention provides methods for the treatment and/or prevention of diabetes as well as the prevention or delay in development of diabetes-related complications, conditions or diseases.

Wellness Enterprises manufactures water filtration and enhancement systems that removes contaminants and also temporarily changes the properties of water by using certain "enhancing media" as a filter to make "enhanced water". The temporary changes in water properties that have been observed include 1) an increase in wetness as compared to unfiltered water (e.g., increased penetration of membranes), 2) an increase in solubility as compared to unfiltered water (solids, liquids, and gases), 3) the release of certain trace minerals from the enhancing media into the enhanced water, most notably silica, magnesium, yttrium, vanadium and titanium, and 4) the release of stabilized negative ions in the enhanced water.

As used herein, the term "wetness" refers to the ability of water molecules to move through a surface (such as biological membranes, tissues, skin, muscle, etc.). Wetness, according to the subject invention, is a function of surface tension and the nature of the surface being wetted. Generally, the surface tension of unfiltered water is higher than enhanced water. The enhanced water of the invention can move more easily through a permeable membrane than unfiltered water. Without being bound by theory, it appears that the enhanced water has decreased surface tension and cohesion between water molecules to enable increased movement through porous membranes (such as tissues and skin). Preferably, the enhanced water of the invention demonstrates increased wetness and ability to move through blood vessels to hydrate blood.

The release of stabilized negative ions is achieved when an electron is released from a water molecule to produce a reduced or "negative" ion. Normally, such ions would be immediately reabsorbed into a water molecule. However, due to the nature of the enhancing media, the enhanced water of the invention causes the release of "stabilized" negative ions from water molecules, wherein the negative ions are not immediately reabsorbed into a water molecule.

In one embodiment, the enhancing media comprises at least one source of silica, at least one material that generates a magnetic field, at least one far infrared emitting material, and at least one igneous rock. In preferred embodiments, the enhancing media comprises: sand or quartz sand as the source of silica; at least one magnet; at least two igneous rocks; and a far infrared ceramic as the far infrared emitting material.

The "enhanced water" of the subject invention has the properties that can be achieved using the Wellness Enterprises water filters. These can include, for example, an increase in wetness and/or solubility, as well as the release of trace minerals and/or negative ions. Filters that can be used according to the subject invention include, for example, the Wellness whole house unit (Model MG-3 or equivalent). Other filters that can be used to produce enhanced water of the invention include those that are disclosed in U.S. Pat. Nos. 5,628,900 and 5,795,471, both of which are hereby incorporated in their entirety.

The subject invention provides methods for treating patients diagnosed with diabetes wherein the patients consume the enhanced water as described herein. In preferred embodiments, the invention provides methods for treating and/or preventing the development of diabetes as well as the complications associated with diabetes. In a specific embodiment, consumption of enhanced water according to the subject invention can be used to reduce the amount of insulin needed by a diabetic.

In another embodiment, the subject invention provides a method for reducing the insulin requirement in a diabetic patient, wherein said method comprises: preparing enhanced water by pouring tap water through a container within which is an enhancing medium comprising a magnet producing at least 4,500 gauss residual flux, a far infrared emitting ceramic, bakuhanseki stone, and a source of silica, wherein contact of said water with the enhancing medium forms enhanced water; and administering to the patient at least four eight-ounce servings of said enhanced water a day.

As used herein, the term "diabetes" is intended to mean all diabetic conditions, including, without limitation, diabetes mellitus, genetic diabetes, type I diabetes, type II diabetes, and gestational diabetes. The term "diabetes" also refers to the chronic disease characterized by relative or absolute deficiency of insulin that results in glucose intolerance. Type I diabetes is also referred to as insulin dependent diabetes mellitus (IDDM) and also includes, for example, juvenile-onset diabetes mellitus. Type I is primarily due to the destruction of pancreatic β-cells. Type II diabetes mellitus is also known as non-insulin dependent diabetes mellitus (NIDDM) and is characterized, in part, by impaired insulin release following a meal. Insulin resistance can also be a factor leading to the occurrence of type II diabetes mellitus. Genetic diabetes is due to mutations which interfere with the function and regulation of β-cells.

Diabetes, as used herein, is characterized as a fasting level of blood glucose greater than or equal to about 130 mg/dl or as a plasma glucose level greater than or equal to about 180 mg/dl as assessed at about 2 hours following the oral administration of a glucose load of about 75 g or following a meal. The term "diabetes" is also intended to include those individuals with hyperglycemia, including chronic hyperglycemia, impaired glucose homeostasis or tolerance, and insulin resistance. Plasma glucose levels in hyperglycemic individuals include, for example, glucose concentrations greater than normal as determined by reliable diagnostic indicators. Such hyperglycemic individuals are at risk or predisposed to developing overt clinical symptoms of diabetes mellitus.

As used herein, the term "diabetic complications" refers to medical/clinical problems that occur more often in patients diagnosed with diabetes. As contemplated herein, diabetic complications include medical/clinical problems that stem from changes in blood vessels and/or nerves as a result of diabetes. These include, and are not limited to, skin conditions (i.e., bacterial infections, fungal infections, diabetic dermopathy, necrobiosis lipoidica, diabeticorum (i.e., bullosis diabeticorum), eruptive xanthomatosis, allergic skin reactions, digital scleroris, disseminated granuloma annulare, and acanthosis nigricans), gum disease, eye disorders (i.e., glaucoma, cataracts, retinopathy, kidney disease, neuropathy (i.e., systemic neuropathy, distal systemic polyneuropathy, proximal neuropathy, femoral neuropathy, neuropathic antrhropathy, cranial neuropathy, authonomic neuropathy, compression neuropathy, and diabetic amyotrophy), and cardiovascular diseases/disorders (i.e., hypertension, heart disease, heart attack, stroke).

The term "patient," as used herein, describes an organism, including mammals, to which treatment with the compositions according to the present invention is provided. Mammalian species that benefit from the disclosed methods of treatment include, and are not limited to, apes, chimpanzees, orangutans, humans, monkeys; and domesticated animals (i.e., pets) such as dogs, cats, mice, rats, guinea pigs, and hamsters.

"Concurrent administration" and "concurrently administering," as used herein, includes administering enhanced water, as described herein, with another compound or therapeutic method suitable for the treatment of diabetes (i.e., insulin and/or a hypoglycemic compound). Preferably, if the enhanced water and the known agent (or therapeutic method) for treating diabetes are administered separately, they are not administered so distant in time from each other that they cannot interact.

The term "effective amount," as used herein, refers to the amount necessary to elicit the desired biological response. In accordance with the subject invention, the effective amount of enhanced water is the amount necessary to treat and/or ameliorate diabetes as well as decrease the severity or prevent a particular diabetes-related complication (i.e., retinopathy, glaucoma, cataracts, heart disease, stroke, hypertension, neuropathy, dermopathy, gum disease, etc.).

Specifically exemplified herein is the use of enhanced water to treat and/or prevent the onset of diabetes in a patient; or to reduce the severity, intensity, or duration of subsequently developed complications related to diabetes. Complications associated with diabetes such as, and not limited to, retinopathy, glaucoma, cataracts, heart disease, hypertension, stroke, gum disease, and dermopathy, can be treated, prevented, and/or reduced through consumption, according to the subject invention, of enhanced water.

Further advantages of the subject invention include treatment and/or prevention of the development of diabetes. Specifically, enhanced water can be administered prior to or upon the diagnosis of diabetes. Alternatively, enhanced water can be administered concurrently with other known agents and/or therapies used to treat diabetes (i.e. insulin, sulfonylureas, biguanides, α-glucosidase inhibitors, thiazolidinediones, meglitinides, D-phenylalanine). In a preferred embodiment, a person drinks at least four 8-ounce glasses of enhanced water per day. Even more preferred is five to twelve 8-ounce servings and most preferred is six to ten 8-ounce servings. In a specific embodiment, insulin usage is improved by drinking at least one serving of enhanced water concurrently with an insulin injection.

Enhanced water can be administered concurrently with insulin to treat type I diabetes, type II diabetes, and related conditions and symptoms. For type II diabetes, insulin resistance, hyperinsulinemia, diabetes-induced hypertension, obesity, or damage to blood vessels, eyes, kidneys, nerves, autonomic nervous system, skin, connective tissue, or immune system, enhanced water may be administered concurrently with a hypoglycemic compound instead of insulin. Alternatively, enhanced water may be administered concurrently with insulin and a hypoglycemic compound to treat type II diabetes, insulin resistance, hyperinsulinemia, diabetes-induced hypertension, obesity, or damage to blood vessels, eyes, kidneys, nerves, autonomic nervous system, skin, connective tissue, or immune system.

Additional compounds and/or therapies with which enhanced water can be administered concurrently include, without limitation, gene-based therapies; insulin and methods for administering insulin (i.e., insulin pump, subcutaneous insulin infusion, via inhaler); sulfonylureas (.e., glyburide, glipizide, glimepiride, tolbutamide, chlorpropramide); insulin secretagogues (i.e., repaglinide, nateglinide); alpha glucosidase inhibitors (i.e., acarbose, miglitol); biguanide; and thiazolidinediones (i.e., rosiglitazone, piaglitazone).

All patents, patent applications, provisional applications, and publications referred to or cited herein are incorporated by reference in their entirety, including all figures, to the extent they are not inconsistent with the explicit teachings of this specification.

Following are examples that illustrate procedures for practicing the invention. These examples should not be construed as limiting.

Example 1

Reduction in Insulin Requirement

A sample of type I diabetics were assembled into a test group. Each one was provided a system that generates the enhanced water of the subject invention, and they were asked to drink this water according to a specified drinking protocol. Each diabetic recorded their daily insulin usage for a period of 90 days.

The specific protocol was as follows:
1. Drink one glass immediately upon rising.
2. Drink one glass approximately 30 minutes before each meal.
3. Drink 2 to 3 glasses in between meals.
4. Drink one glass approximately 2 hours after the last meal of the day.

At the end of the study, many of the participants showed a consistent decline of daily insulin usage until a new average daily level was reached. Some of the reductions were very substantial (40% to 80% declines) and were totally unexpected. At the end of the study, many of the participants showed a consistent decline of daily insulin usage until a new average daily level was reached. Some of the reductions were very substantial (40% to 80% declines) and were totally unexpected. A glass for this study was considered to be about 10 to 12 ounces.

Example 2

Improved Hydration

Diabetics (type I and type II) who drank the enhanced water of the subject invention had an improvement in the hydration of their blood (diabetics tend to be dehydrated and their blood cells are somewhat flaccid and less mobile than non-diabetic blood) and an improvement in their blood circulation. This was observed by first viewing diabetic blood under a microscope and recording the shape and mobility of the blood. Subjects were given a controlled amount of water to drink and then a secondary blood sample was draw 30 minutes later and observed. Subjects were tested twice in this fashion; once with enhanced water and secondarily with tap water. The subjects' blood was not observed to be any different 30 minutes later after drinking the tap water but the same subjects were observed to have more fully hydrated blood and more mobile blood when observed 30 minutes after drinking the enhanced water.

Example 3

Method for Producing Enhanced Water

In one embodiment, the water used according to the subject invention is produced by a process involving purifying water followed by enhancement. The purification may consist of one or more of the following known processes for water purification: carbon filtration, reverse osmosis, ceramic filtration, ionic exchange, ionic absorption and distillation. The purification stage may consist of one or more steps to remove dissolved and suspended materials that may be considered harmful to the body such a chlorine, chloramine, heavy metals, radioactive compounds, bacteria parasitic cysts, volatile organics, solvents, pesticides and any compound that may be consider as a free radical or produce a so called free radical attack on the body.

The enhancement stage can comprise one or more of the following steps: 1) exposing the water to a source of silica such as sand or quartz sand; 2) exposing the water to a magnetic field (this may be done either indirectly or directly such as practiced by Naito in U.S. Pat. Nos. 5,628,900 and 5,795,471, which are incorporated herein, in their entirety, by reference); 3) contacting the water with a far infrared emitting material such as far infrared ceramics; 4) contacting the water with an igneous rock such as Bakuhan™ stone; and 5) contacting the water with an igneous rock such as Taicho™ stone.

Additional steps can also be utilized; for example, the process can be further enhanced by increasing the number of magnetic stages and far infrared-emitting media stages. The process can also be further enhanced by adding a sixth stage of quartz crystals.

Example 4

Apparatus for Producing Enhanced Water

A device used for producing enhanced water of the subject invention can consist of a container with a conduit at both ends for the purpose of communicating water into, through, and out of the container. The container is equipped with entrance and exit filters, screens or separators that allow the passage of water through the container without allowing the release or escape of the materials contained within the container. Inside the container are a plurality of uniquely separated contact materials. These materials may be, for example, 1) a layer of material providing a source of soluble silicon such as sand or quartz;, 2) a magnet; 3) a layer of magnetite granules; 4) a layer of far infrared emitting materials such as far infrared ceramics; 5) a layer of igneous stone such as bakuhanseki stone; and a second layer of igneous stones such as taichoseki stone.

Example 5

Increased Wetness of Enhanced Water

Unfiltered water was flushed through the device of Example 4 for approximately 6 minutes at a flow rate of approximately 4 litres/minute and the resultant enhanced water was collected. A 45 mL aliquot of the enhanced (or treated) water was poured into a plastic vial for sampling. A second 45 mL aliquot of unfiltered (or untreated) water was poured directly into a second vial for sampling. Portions of the two samples were analyzed for composition by oxygen-17 NMR spectroscopy on a Bruker AVANCE AV300 spectrometer (Rheinstetten, Germany) according to procedures described in WSH003/2299/1.

Comparison of oxygen-17 NMR half-height line widths after NMR spectrometer analysis indicate that the enhanced water was measurably narrower than that of tap water (see Table 1 below). The results are provided in hertz (Hz) frequency, which indicates the size of water molecule clusters formed as a result of cohesive forces/electrostatic bonds. A lower Hz frequency represents smaller water molecule clusters. With smaller water molecule clusters (or reduced cohesive forces; weak electrostatic bonds), there is an increased ability for the water to permeate (or pass through) surfaces. As demonstrated below, the enhanced water of the invention demonstrates increased wetness when compared to untreated water.

TABLE 1

NMR Spectrometer Results

| Sample ID | Description | O-17 Linewidth at Half Height |
|---|---|---|
| C2299/1 | Treated tap water after passing through Wellness enhanced filter | 64 ± 2 Hz |
| C2299/3 | Untreated tap water | 86 ± 2 Hz |

Example 6

Increased Solubility in Enhanced Water

Unfiltered water was flushed through the device of Example 4 for approximately 5 minutes at a flow rate of approximately 4 litres/minute and the resultant enhanced water was collected. A 40 mL aliquot of enhanced (treated) water was poured into a plastic vial for sampling. A second 40 mL aliquot of untreated tap water was poured directly into a second vial for sampling. After equilibration of the water at 25° C., 900 μL of corn oil was added and the mixture shaken for 5 minutes on a mechanical shaker, then allowed to separate for 10 minutes. Portions of the samples were analyzed for composition by proton NMR spectroscopy at 25° C. on a Bruker AVANCE AV300 spectrometer (Rheinstetten, Germany) according to procedures described in WSH003/2312/1. NMR analysis was conducted sequentially after each sample was shaken and allowed to separate, with each water sample experiencing the same equilibration temperature, shaking time, standing time, and time in the NMR spectrometer.

Comparison of proton NMR concentrations of suspended corn oil (see Table 2 below) indicate that the concentration of oil in the enhanced water was measurably higher than that in the untreated water. The untreated water was used as a reference standard and give a value of 1.0. Because there was a greater concentration of oil in the enhanced water as compared to the untreated water, greater solubility of oil in water is demonstrated with the enhanced water.

TABLE 2

NMR Concentration Results

| Sample ID | Description | Corn Oil Content (relative to tap water) |
|---|---|---|
| C2312/1 | Water treated with Wellness Enhanced Filter | 1.78 |
| C2312/3 | Untreated water | 1.00 |

It should be understood that the examples and embodiments described herein are for illustrative purposes only and that various modifications or changes in light thereof will be suggested to persons skilled in the art and are to be included within the spirit and purview of this application.

I claim:

1. A method for reducing the insulin requirement in a diabetic patient, wherein said method comprises: preparing enhanced water by pouring tap water through a container within which is an enhancing medium comprising a magnet producing at least 4,500 gauss residual flux, a far infrared emitting ceramic, bakuhanseki stone, and a source of silica, wherein contact of said water with the enhancing medium forms enhanced water; and administering to the patient at least four eight-ounce servings of said enhanced water a day.

2. The method of claim 1, wherein the enhanced water has any one or combination of the following properties: increased wetness; greater solubility of solids, liquids, and gases in the enhanced water; and presence of trace minerals.

3. The method of claim 2, wherein the trace minerals are selected from the group consisting of magnesium, yttrium, vanadium, and titanium.

4. The method of claim 1, further comprising the step of concurrently administering other agents or therapies used to reduce the insulin requirement in a diabetic patient.

5. The method of claim 1, wherein the enhanced water is administered using the following protocol: (a) at least one serving of the enhanced water immediately upon rising; (b) at least two to three servings of the enhanced water in between meals; and (c) at least one serving of the enhanced water approximately two hours after the last meal of the day.

6. The method of claim 5, wherein step (b) comprises drinking at least one serving of the enhanced water about 30 minutes before each meal.

7. The method of claim 1, further comprising the step of purifying the tap water first prior to pouring the water into the container.

8. The method of claim 7, wherein the purifying step is a process for water purification that includes one or more of the group consisting of: carbon filtration, reverse osmosis, ceramic filtration, ionic exchange, ionic absorption, and distillation.

9. The method of claim 1, wherein the silica is sand or quartz sand.

* * * * *